United States Patent [19]
Graybill et al.

[11] Patent Number: 4,619,259
[45] Date of Patent: Oct. 28, 1986

[54] OPHTHALMIC SURGERY TOOL

[76] Inventors: Walter R. Graybill, 4585 Auhay Dr., Santa Barbara, Calif. 93111; Jeffery J. Graybill, 441 E. Camino Collegio, Santa Maria, Calif. 93454

[21] Appl. No.: 148,258

[22] Filed: May 9, 1980

[51] Int. Cl.$^4$ .............................................. A61B 17/32
[52] U.S. Cl. .................................................. 128/305
[58] Field of Search ............ 128/305, 305.1, 751–754, 128/253, 302, 315; 30/315, 294

[56] References Cited

U.S. PATENT DOCUMENTS

| | | | |
|---|---|---|---|
| 3,074,407 | 1/1963 | Moon et al. ................ | 128/303 R |
| 4,205,682 | 6/1980 | Crock et al. ................ | 128/305 |
| 4,526,171 | 7/1985 | Schachar ...................... | 128/305 |

FOREIGN PATENT DOCUMENTS 2849011  6/1979  Fed. Rep. of Germany ...... 128/326

Primary Examiner—Michael H. Thaler
Attorney, Agent, or Firm—Jack C. Munro

[57] ABSTRACT

An ophthalmic surgery tool which takes the form of an apparatus which is to simultaneously produce a plurality of cuts within the cornea of an eye in order to improve vision. The surgery tool includes a cutter assembly which is movably mounted in respect to a base. The extent of movement of the cutter assembly is predetermined to preclude excessive cutting. Movement of the cutter assembly is due to movement structure which may either be mechanical or fluid operated.

1 Claim, 8 Drawing Figures

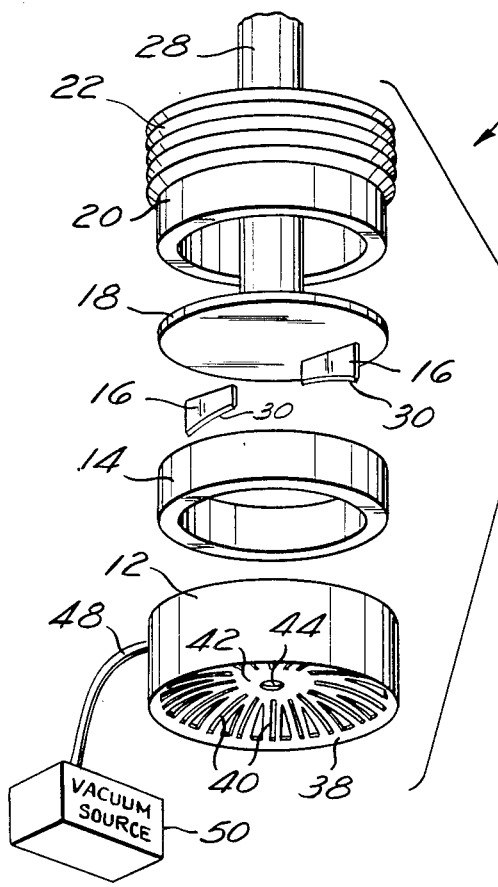
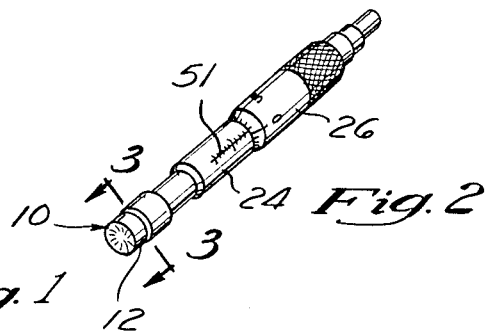
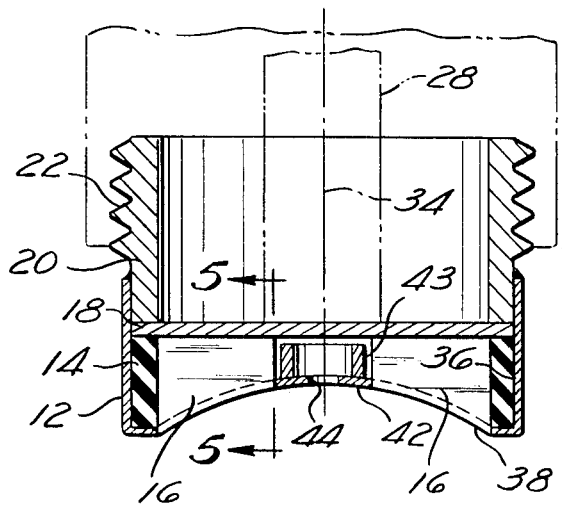
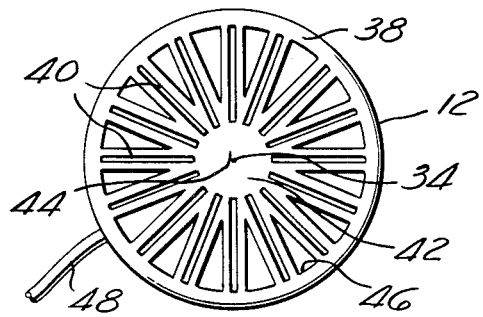
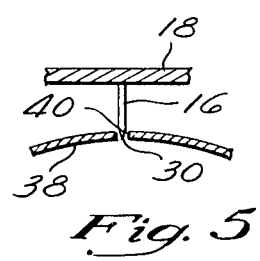
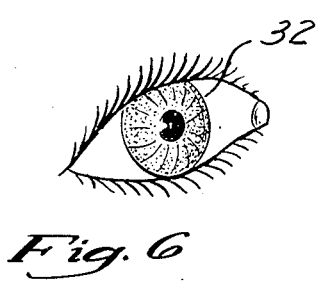
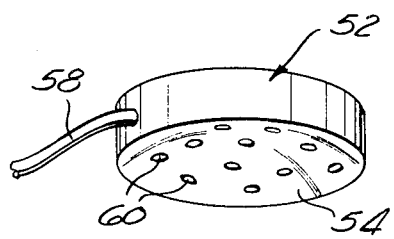
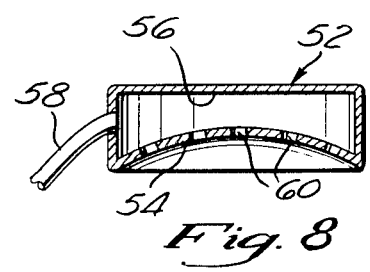

OPHTHALMIC SURGERY TOOL

BACKGROUND OF THE INVENTION

The field of this invention relates to surgery tools and more particularly to a tool which is to facilitate surgery of the eye for the purpose of improving vision.

Nearsightedness is generally believed to be a heritary condition that results in an abnormal focus of the eye partly due to the shape of the cornea (the frontal surface of the eye through which light rays pass). When this condition exists, images come to focus within the eye rather than at the retina (near the back edge of the eye). This allows only those objects that are close to be seen clearly when the image is transmitted by the eye's optic nerve from the retina to the brain.

There is a new microsurgical technique known as a radial keratotomy which consists of making a series (generally sixteen in number) radial incisions, three to four millimeters long, in the surface of the cornea. These incisions flatten the cornea, altering the path of the light waves and moving the focus back to the retina resulting in clearer vision. It is not at all uncommon for an extremely nearsighted individual, after this surgical technique, to have vision of 20/20 (or close thereto) which is commonly deemed to be the most desirable vision.

Currently, this surgical technique is performed with the surgeon making the required plurality of cuts individually. These cuts must be made with a high degree of precision. Specifically, the depth of the cuts has to be very closely controlled as well as the length of the cut and the position of the cut. This is difficult to do by hand by even the most experienced and competent surgeon. Also, it appears that the most desirable number of cuts is approximately sixteen in number. Such individual precise forming of such a large number of cuts is a very time consuming procedure. Surgery time is most expensive.

There is a definite need for the use of a tool which could precisely create the desired number of cuts within an eye with a minimum amount of time. Also, it would be desirable if the tool could be employed by individuals which do not necessarily have the highest degree of surgical skill.

SUMMARY OF THE INVENTION

The surgery tool of this invention is directed to a device which is to be mounted directly onto the eye. The part that is mounted directly on the eye is referred to as the locating base. The surface directly in contact with the eye has a plurality of spaced-apart slits with the slits being radially located in respect to the center of the locating base. Each slit is spaced a predetermined identical distance from the center. It is most desirable to have the slits be equiangularly spaced apart. A cutting blade is to be associated with each slit. The cutting blades are securely mounted on a plate. The plate is held in an at rest position with the cutting blades retracted, that is, the cutting blades do not protrude exteriorly of the locating base. The locating base also includes a plurality of suction openings. The interior of the locating base is to be conducted with a vacuum which is then conducted through the suction openings tending to maintain the eye in tight contact with the surface of the locating base. An actuating means for moving the cutters simultaneously to an extended position is to be provided. This actuation means may take the form of a mechanical means, such as a screw thread micrometer-type movement structure, or can take the form of a pneumatic or hydraulic actuator. Incorporated between the plate supporting the cutting blades and the locating base is a stop assembly to limit the extended movement of the cutting blade. A separate cast may be employed after the cutting operation to position and maintain the eye in a predetermined position to cause such to remain in that position until the healing process is initiated.

The primary objective of this invention is to construct a tool to facilitate the performing of an operation on the eye known as a radial keratotomy.

BRIEF DESCRIPTION OF THE DRAWING

FIG. 1 is an exploded isometric view of the ophthalmic surgery tool of this invention;

FIG. 2 is an isometric view of the assembled surgical tool of this invention showing such being attached to an example of a type of actuator employed in conjunction therewith;

FIG. 3 is a cross-sectional view through the cutting blade assembly employed within the ophthalmic surgery tool of this invention;

FIG. 4 is a bottom plan view of the ophthalmic surgery tool of this invention;

FIG. 5 is a cross-sectional view depicting the movement of a single cutting blade of the ophthalmic surgery tool of this invention;

FIG. 6 is a diagramatic illustration of an eye which has been cut using the tool of this invention;

FIG. 7 is an isometric view of a type of eye cast which may be employed after performing surgery using the tool of this invention upon the eye; and FIG. 8 is a cross-sectional view through the cast of FIG. 7.

DETAILED DESCRIPTION OF THE SHOWN EMBODIMENT

Referring particularly to the drawing, there is shown the ophthalmic surgery tool 10 of this invention which is constructed primarily of a locating base 12, a ring 14, a plurality of cutting blades 16, a base 18 and an attaching sleeve 20. The attaching sleeve 20 includes a series of threads 22. The function of the threads 22 is to facilitate attachment to an appropriate actuation means. The actuation means shown within FIG. 2 comprises a mechanical type of actuator which comprises a fixed sleeve 24 and a rotatable sleeve 26. The rotatable sleeve 26 is connected to the fixed sleeve 24 through a screw thread arrangement (not shown). Attached to the rotatable sleeve 26 and extending through the interior of fixed sleeve 24 is an actuator rod 28. The actuator rod 28 passes through the interior of the sleeve 20 and abuts plate 18. It is to be understood that other types of actuating means could be employed, such as a hydraulic or a pneumatic type of actuating assembly.

Fixedly attached to the lower surface of the plate 18 are a plurality of cutting blades 16. Each cutting blade 16 is identical to each other and there will normally be sixteen in number of blades 16. However, it is considered to be within the scope of this invention that a smaller number of blades 16 could be employed as well as a larger number of blades 16.

Each of the blades 16 are very thin and are actually only a few thousanths of a millimeter thick and about three or four millimeters long. The cutting edge 30 of each cutting blade 16 is convexly formed and is designed to be formed to the exterior surface of a human eye 32. The cutting blades 16 are equiangularly spaced apart. Also, each cutting blade is spaced the same distance away from a center axis 34.

The plate 18 rests on the ring 14. The ring 14 is designed to be of non-metallic material, such as rubber or other type of resilient material. The ring 14 is mounted within an internal chamber 36 formed within the locating base 12. The size of the ring 14 is selected so that at the normal at rest position, the cutting blades 16 will be totally located in the retracted position, that is, within the internal chamber 36. Pressure exerted against the plate 18, by means of the downward movement of the rod 28, causes a slight compressing of the ring 14 and protruding of the cutting edges 30 exteriorly of the surface of the locating base 12.

The surface 38 is convexly formed substantially the shape of the outer surface of the eye 32. The surface 38 includes sixteen in number of slits 40. Each slit 40 is to connect with a cutting blade 16 as generally depicted within FIG. 5 of the drawing. The surface 38 includes a central hub section 42 which only includes a central opening 44. The purpose of the central opening is to facilitate centering of the locating base 12 upon the eye 32. The size of the hub section 42 is for the purpose of covering entirely the corneal cap of the eye 32. Also located within the surface 38 are a plurality of suction openings 46.

A conduit 48 passes through the exterior wall of the locating base 12 and connects with the internal compartment 36. Conduit 48 is to connect with a vacuum source 50. Vacuum is to be supplied through the conduit 48 within the internal chamber 36 and out through the openings 46 tending to tightly hold the exterior surface of the eye 30 in tight contact with the surface 38. The amount of vacuum required is to be quite small and normally not exceeding one pound per square inch.

It is to be understood that the number and selection of the openings 46 is deemed to be a matter of choice. In actual practice, possibly the openings 46 could even be eliminated with the vacuum being conducted in the slight space between each of the slits 40 and their respective blade 16.

Fixedly mounted on the inside of the hub section 42 is a stop member 43. This stop member 43 will generally comprise an annular sleeve. The upper surface of the stop member 43 is to contact the plate 18 and when this occurs, the movement of the blades 16 exteriorly of the surface 38 have been limited. This limiting of the movement of the blades 16 is so as to prevent excessive depth cutting by the blades 16. The exact depth of cut must be precisely controlled for each patient. For example, for one particular patient, a twenty thousanth of an inch depth would be satisfactory, where for another patient, only a sixteenth thousanths of an inch depth of cut would be satisfactory.

The operation of the surgery tool 10 of this invention is as follows: Prior to the locating on the eye 32, the physician has moved the actuator by rotating sleeve 26 until the tip 30 of the blades 16 are in alignment with the surface 38. The physician then notes this position, such as by means of indicia 51 on sleeve 24, and then reversely rotates the sleeve 26 a predetermined amount, such as five thousanths of an inch. This means that the blades 16 are now retracted five thousanths of an inch within the internal compartment 36.

The assembled surgical tool, as shown in FIG. 2, is then to be mounted directly upon the eye 32 and centrally located with respect to the corneal cap of the eye 32. In other words, the axis 34 will be aligned with the center of corneal cap. The physician at that time then activates the vacuum source 50 which causes the surface 38 to be fixedly held in position with respect to the eye 32. The physician now begins the surgical procedure.

The physician rotates the sleeve 26 forward the five thousanths of an inch so the tip 30 of the cutting blade 16 are now again aligned with the surface 38. The physician then proceeds to rotate the sleeve 26 a predetermined precise amount, such as twenty thousanths of an inch causing the tip 30 of each of the sixteen blades 16 to cut into the corneal epithelium and into the endothelium. This cutting procedure may be facilitated by imparting a fine vibrational (such as a sonic vibration) movement to the blade 16. In such an instance, appropriate vibration means would be employed (not shown). The reason for the vibrational cutting means is that the corneal epithelium is extremely durable. The stop 43 will prevent accidental excessive movement of the cutting blades 16.

The physician then reversely rotates sleeve 36 so as to cause the cutting blades 16 to be retracted. The vacuum source 50 is turned off and the locating base 12 removed from contact with the eye. The surgical procedure at this time has now been completed, the sixteen cuts having been simultaneously formed within the eye 32.

It is to be understood that there will be a variety in number employed of locating bases 12 with the convavity of each base 12 being varied. The physician is to select the particular concavity of the base 12 which is closest to the shape of the particular patient's eye. It is estimated that there will be somewhere around a dozen different shapes of locating bases 12.

After the surgical procedure has been performed, it may be desirable in some instances to position the eye 32 in a particular position and maintain that shape for a particular period of time. The normal period of time would be until the healing process has initiated. This position of the eye 32 has been predetermined for the particular patient as being the most desirable shape so that the patient will achieve the best possible vision. To so locate the eye, the physician selects a particular shape of cast 52 with it being understood that there will be available a variety of different shapes of casts 52. The cast 52 has a concave surface 54 similar to the concave surface 38. The cast 52 includes an enclosed internal chamber 56. The suction conduit 58 connects to the internal chamber 56. Surface 54 includes a plurality of holes 60 formed therein. The surface 54 is to be centrally positioned in the manner of positioning of surface 38 upon the eye 32. The operator then draws the vacuum through the vacuum source 50 through the conduit 58 to within the internal chamber 56. The cast 52 is then maintained in this position on the eye 32 for a certain period of time, such as three or four hours. Hopefully, after removal of the cast 52, the eye 32 will remain in the established position.

What is claimed is:

1. An ophthalmic surgery tool for producing a series of cuts within the cornea of an eye for the purpose of improving vision, said surgery tool comprising:

a locating base, the exterior surface of said locating base being recessed to closely conform to the exterior surface of the eye, said locating base having an internal chamber, said locating base having a longitudinal center axis, said locating base having a plurality of spaced apart first openings formed within said exterior surface;

a cutter assembly, said cutter assembly located within said internal chamber and mounted in conjunction with said first openings, said cutter assembly being symmetrically arranged about said longitudinal center axis, said cutter assembly being movable in respect to said locating base between a retracted (non-cutting) position and an extended position, said retracted position locating said cutter assembly substantially entirely within said internal chamber, said extended position connecting said cutter assembly with said first openings with a portion of said cutter assembly conducted through said first openings protruding exteriorly of said locating base;

means connected to said cutter assembly for moving said cutter assembly between said retracted position and said extended position;

vacuum means connected to locating base, said vacuum means for applying a vacuum within said internal chamber;

biasing means located between said locating base and said cutter assembly, said biasing means exerting a continuing bias against said cutter assembly tending to locate such in said retracted position, said biasing means comprising a ring of resilient material; and second openings formed within said locating base, there being a said second opening located between each directly adjacent pair of said first openings, said vacuum to cause a slight suction force to be created between said locating base and the eye thereby holding the eye tightly against said locating base directly in the proximity of said cutter assembly.

* * * * *